United States Patent [19]
Pankratz

[11] Patent Number: 4,810,639
[45] Date of Patent: Mar. 7, 1989

[54] IMMUNOASSAY FOR CK-MB USING BOUND AND SOLUBLE ANTIBODIES

[75] Inventor: Thomas J. Pankratz, Newark, Del.

[73] Assignee: E. I. Du Pont de Nemours and Company, Wilmington, Del.

[21] Appl. No.: 852,708

[22] Filed: Apr. 16, 1986

Related U.S. Application Data

[63] Continuation-in-part of Ser. No. 811,783, Dec. 20, 1985, abandoned.

[51] Int. Cl.[4] ............................................. G01N 33/53
[52] U.S. Cl. .................................... 435/7; 435/174
[58] Field of Search ........................................ 435/7

[56] References Cited

U.S. PATENT DOCUMENTS

| | | | |
|---|---|---|---|
| 4,067,775 | 1/1978 | Wurzburg et al. | 435/7 |
| 4,260,678 | 4/1981 | Lepp et al. | 435/7 |
| 4,267,271 | 5/1981 | Roberts | 435/7 |
| 4,353,982 | 10/1982 | Gomez | 435/7 |
| 4,376,110 | 3/1983 | David et al. | 436/513 |
| 4,387,160 | 6/1983 | Gomez et al. | 435/7 |
| 4,624,916 | 11/1986 | Shah | 435/7 |

OTHER PUBLICATIONS

Jockers-Wretou et al., Clin. Chem. Acta, 58, 223 (1975).

Primary Examiner—Sam Rosen
Attorney, Agent, or Firm—George A. Frank

[57] ABSTRACT

An immunoassay for CK-MB is provided based on the sequential immunoinhibition first by an immobilized and then by a soluble antibody of either the CK-M or the CK-B sub-units in CK-MM, CK-MB aned CK-BB, followed by an enzymatic determination of the unbound sub-unit in CK-MB (the unbound CK-BB or CK-MM having been previously removed).

22 Claims, No Drawings

4,810,639

IMMUNOASSAY FOR CK-MB USING BOUND AND SOLUBLE ANTIBODIES

RELATED APPLICATIONS

This application is a continuation-in-part of application Ser. No. 811,783, filed Dec. 20, 1985, now abandoned.

TECHNICAL FIELD

This invention relates to the determination of creatine kinase isoenzymes in a sample via the measurement of activities of immobilized antibody-isoenzyme complexes. More specifically, using bound and soluble antibodies, the substantially complete immunoinhibition of immobilized creatine kinase M or B sub-unit is achieved, followed by the determination of enzymatic activity of the immobilized creatinine kinase B or M sub-unit, respectively.

BACKGROUND ART

Three predominant isoenzymes of creatine kinase (CK; E.C. 2.7.3.2) are recognized; these are dimers consisting of the M and B sub-units. These dimers may comprise two M or two B sub-units, or one M and one B sub-unit. The predominant dimer present in the blood, serum, or plasma of normal individuals is CK-MM isoenzyme, with variable but usually only trace quantities of CK-MB that reflect the normal degradation of skeletal muscle. The CK-BB isoenzyme is not usually present in detectable amounts in serum of normal persons but is present in significant quantities in brain tissue and smooth muscle. Elevations of the BB isoenzyme can occur in pathologic conditions such as metastatic carcinoma or severe burns. The presence of elevated levels of CK-MB isoenzyme has been used as a clinically important indication of myocardial infarction in instances where possible sources of significant skeletal muscle damage can be eliminated. More particularly, repetitive determinations of CK-MB level in the serum can indicate the time course and severity of infarctions. Differentiation between the isoenzymes of creatine kinase, therefore, is clinically important and the availability of a rapid, efficient, and highly discriminatory assay for the CK isoenzymes was needed.

Several approaches to analysis of the CK isoenzymes have been used in the past which rely either upon physical separation of the isoenzymes with subsequent identification, or upon highly selective reactions between the isoenzymes and antibodies. Physical separation methods such as electrophoresis or column chromatography are time consuming, require considerable skill, and are frequently incapable of highly reproducible separations to resolve adequately the isoenzymes with sufficient sensitivity to monitor early changes in CK-MB levels. The inconvenience of physical separation techniques and their inability to unequivocally resolve CK isoenzymes lead to immunochemical techniques which, based upon their unique structural or immunochemical determinants, have the potential to differentiate between the isoenzymes in complex mixtures.

Jockers-Wretou et al., Clin. Chem. Acta Volume 58,223 (1975), used an immunoprecipitation method with antisera elicited in rabbits by the crystallized MM and BB isoenzymes from human muscle and brain tissue, respectively. Both forms of isoenzyme were quantitatively precipitated from tissue extracts and serum without measurable cross reaction. The CK-MB isoenzyme reacted to some degree with both antisera, but not completely with either. It was also demonstrated that the CK-MM isoenzyme activity was completely inhibited after reaction with anti-CK-MM antibody. The CK-MB isoenzyme activity was inhibited by 80% when reacted with either anti-CK-BB or anti-CK-MM antiserum. The CK-BB isoenzyme was not completely inhibited by binding to anti-CK-BB antibody, but could be completely removed by centrifugation. Therefore, the combination of selective immunoprecipitation and immunoinhibition of the isoenzymes allowed their differentiation, but the process required separate centrifugations and more than one activity assay to determine the relative contributions of the isoenzymes, particularly the CK-MB activity, by comparison to CK-MM and CK-BB samples. In addition, about 10% of the CK-MB activity was neither precipitable nor inhibitable by the disclosed procedures, which introduced error into enzyme sub-unit estimates.

U.S. Pat. No. 4,067,775, issued Jan. 10, 1978 to Wurzburg et al., discloses an immunoinhibition assay for CK-MB in which antibodies capable of completely inhibiting the M sub-unit activity were combined with an appropriate sample in solution. The mixture was allowed to react for sufficient time to substantially or completely inhibit the M sub-unit and the residual enzyme activity in the solution was determined. This method represented an advancement by use of a non-precipitating antibody which obviated the need for long incubations and centrifugations, and also made possible direct testing of the uninhibited B sub-unit in solution without additional sample processing. This approach offers speed and simplicity, but is subject to the disadvantage that, because the B sub-unit is essentially uninhibited, any contaminating BB isoenzyme in the sample can provide a source of error in those instances where concentrations are significant. A typical CK isoenzymes, such as mitochondrial or macro CK types 1 and 2, can also provide sources of error. The activity contributed by adenylate kinase must be determined in a separate reaction medium which lacks phosphocreatine, which is the normal CK substrate, and this activity value has to be subtracted from the antibody-treated reaction mixture activity value. These various elements introduce sources of error in the determination of CK-MB activity and require additional control assays to blank contaminating adenylate kinase activities.

U.S. Pat. No. 4,260,678, issued Apr. 7, 1981 to Lepp et al., discloses a CK assay using immobilized antibodies to either the CK-M or CK-B sub-unit, or both. The selected antibody, which did not inhibit or substantially change the activity of the bound sub-unit, was immobilized on a carrier such as porous glass beads and then reacted with sample followed by the separation of the immobilized antibody-isoenzyme complexes from the reaction mixture prior to determination of enzyme activity of sub-units bound to the carrier. This approach is useful to determine total activity by reacting both anti-CK-M and anti-CK-B carriers with sample, or of individual sub-units by reaction of one or the other carrier with sample. This method allows separation of desired isoenzymes from contaminating forms, such as macro-CK, but also requires multiple assays with subtraction of results to determine activity associated with each sub-unit type. It is not possible to determine the activity associated with the hybrid dimer CK-MB using this approach. Therefore, the technique has limited utility in a clinical laboratory.

U.S. Pat. No. 4,387,160, issued June 3, 1983 to Gomez et al., discloses an assay for CK-MB which uses three separate antibody preparations and two separate assays on a given sample. In one assay, an anti-CK-M antibody capable of substantially or completely inhibiting the M sub-unit activity, without significantly affecting B sub-unit activity, is combined with one portion of a sample and allowed to react. If precipitation occurs during this reaction, the precipitate will remain homogeneously suspended during the process of this reaction. The residual isoenzyme activity in this solution is determined by conventional means. A second portion of sample containing at least CK-M sub-units is reacted with an anti-CK-M antibody and the complexes so formed are further reacted with a precipitating second antibody capable of reacting with determinants on the anti-CK-M antibody. The precipitate is separated from the reaction mixture and residual activity, presumably representing B sub-unit remaining in the supernatant, is determined by conventional means. Activity from the second sample representing contaminating B sub-units is subtracted from the activity of the first sample, which represents both MB and contaminating B sub-units, to determine MB activity. This assay combines immunoinhibition with precipitation techniques to determine CK-MB levels in samples, but does so with considerable inconvenience in time-consuming processing steps and with several, highly specialized reagents.

Finally, sandwich immunoassays employing the two-site immunometric approach to measure mass concentrations, not enzymatic activity, see U.S. Pat. No. 4,376,110, issued Mar. 8, 1983, can be used to detect CK-MB by immobilizing all M or B-containing sub-units onto a solid phase by binding to a monoclonal antibody specific for one sub-unit that is itself covalently attached to the solid phase. The desired sub-unit is detected by binding with a labelled second monoclonal antibody specific for that sub-unit. The amount of label, such as enzyme activity, is a direct measure of the concentration of the desired sub-unit in the original sample. This approach requires two highly specific reagents, one labelled with an appropriate indicator enzyme, and can be subject to an elevated number of false positive results owing to the interaction of the enzyme-labelled second antibody with the solid support in a nonspecific manner. This disadvantage can be overcome by the analysis of inherent CK sub-unit acitivity to determine levels of CK-MB under appropriate circumstances.

There is a need for a CK-MB assay that can provide simply, precisely, and economically an accurate evaluation of the CK-MB hybrid dimer level in body fluids of individuals suspected of suffering from acute myocardial infarction.

DISCLOSURE OF THE INVENTION

The immunoinhibition assay of this invention comprises:
(a) forming a first reaction mixture by contacting a liquid sample suspected of containing CK-MB isoenzyme with a molar excess of either anti-CK-M or anti-CK-B sub-unit antibody immobilized on a solid phase, said antibody being capable of substantially completely inhibiting the enzymatic activity of the bound sub-unit;

(b) allowing a reaction to occur whereby complexes are formed between M or B sub-unit-containing isoenzymes and the immobilized antibody;
(c) separating the solid phase from the reaction mixture;
(d) forming a second reaction mixture by contacting the solid phase with a soluble anti-CK-M or anti-CK-B sub-unit antibody with the same sub-unit specificity as said immobilized antibody, capable of substantially completely inhibiting the enzymatic activity of the bound sub-unit; and
(e) determining the enzymatic activity of the uninhibited isoenzyme associated with the solid phase.

DESCRIPTION OF THE INVENTION

The method of this invention is capable of determining specifically the enzymatic activity of creatine kinase-MB (CK-MB) isoenzyme in liquid samples in a rapid, simple, efficient, and economical manner. Liquid samples include whole blood, serum, plasma, cerebrospinal fluid, urine, pleural and lymphatic fluids, and any other biological fluid suspected of containing CK-MB isoenzyme. Particulate materials which may be of interest, such as biopsies of appropriate organ systems, can be extracted by known methods which preserve the activity of CK-MB isoenzymes and the extracts analyzed by the method.

An important aspect of this invention is the preparation of an appropriate anti-CK-M or anti-CK-B antibody, which is capable of binding with M or B sub-units, respectively, and of substantially completely inhibiting the activity of the bound sub-unit. It is a further requirement that the anti-CK-M or anti-CK-B activity inhibiting antibody will not substantially affect the enzymatic activity of the sub-unit associated with the bound sub-unit of CK-MB.

These antibodies can be obtained by known methods. A suitable inhibiting anit-CK-M sub-unit has been described in U.S. Pat. No. 4,067,775, incorporated herein by reference. For example, the crystallized CK-MM antigens from skeletal muscle tissue of vertebrates, preferably that of human origin, is innoculated into an immunocompetent hose according to an appropriate schedule which causes the amount of circulating antibodies reactive with the antigen to increase. Antigen sources may be selected from skeletal muscles of various animals such as monkeys, chimpanzees, apes and domestic animals such as pigs, sheep, cattle, horses, donkeys, rabbits and guinea pigs. Other animals such as rats, mice and birds can also be used. The immune serum can be harvested and used directly following appropriate activity determinations, or antibodies can be purified from animal immune serum by known methods. The purified antibodies can be used whole, or can be fragmented by enzyme digestion using papain, pepsin, etc., to produce monovalent or divalent partial antibodies, respectively. Whole antibody purified from immune serum is preferred. Alternatively, immune lymphocytes can be obtained from the host animal and when these lymphocytes are fused with appropriate immortal cells, such as myeloma cells, they will produce hybridoma cells capable of secreting desired monoclonal antibodies. These techniques are familiar to those skilled in the art; a more complete description can be found in Mayer et al., Immunochemical Methods in the Biological Sciences: Enzymes and Proteins, Academic Press, London, 1980, p. 5–17.

The particular animal source, antibody isotype, and whether whole or partial antibody is used are not critical in the carrying out of the method of this invention as long as certain criteria are met. The selected antibody must be capable of binding to the appropriate CK sub-unit and remain associated with it throughout several washing procedures and isoenzyme activity determinations. This requirement is met most readily by those antibodies with affinity constants of at least $10^6$ liters/mole, preferably $10^7$ liters/mole, and most preferably $10^9$ liters/mole. The antibody must also be capable of substantially completely inhibiting the enzymatic activity of the bound sub-unit. For example, in a typical sample containing 200 U/L, no more than 10 U/L of residual sub-unit activity should remain after antibody binding, and preferably not more than 5 U/L of activity will remain.

The immobilization procedure for attaching antibody to an appropriate solid phase needs to be selected carefully. The procedure should be sufficiently mild to preserve both the binding and inhibiting abilities of the antibody in reactions with the appropriate isoenzyme sub-unit but result in a stable product to withstand the immunoassay conditions. Covalent attachment of the antibody to the solid phase is expected to be the most stable and can be accomplished by known methods (see e.g., European Patent Application 88,695, published Sep. 14, 1983, in Bulletin 83/37). Under some circumstances, antibody adsorbed onto or ionically associated with the surface of appropriate solid phases may be sufficiently resistant to removal by exchanges of reaction mixtures and wash solutions. It is also expected that noncovalent associations of antibodies with binding proteins such as Protein A or anti-antibody, which do not interfere with the abilities of anti-CK sub-unit antibody to bind and inhibit the isoenzyme sub-unit, can be used to prepare immobilized antibodies necessary for the immunoassay of this invention.

The solid phase on which the antibody is immobilized can be organic or inorganic, porous or non-porous and in any desired shape or form. The solid phase can be particulate having its physical properties such as density, surface area, diameter, selected to meet the needs of a particular assay application. Particles which require large concentrations of antibody attached and which must be in maximum contact with antigen in reaction mixtures over extended periods can be selected from those particles which have large surface area to volume ratios, accessible, reactive functional groups for antibody attachment, and also have densities approaching that of the suspending medium to prevent settling. Small particle diameters, to provide a high surface area per volume of particulate reagent dispensed, are preferred. Alternatively, the solid phase can be shaped in any desired form such as in flat sheets, cylindrical shafts, circular wafers, or rectangular or cuboidal blocks to conform with specifications of manual or automated systems which are designed to move reaction mixtures into and out of contact with the solid phase. The solid phase can be selected to be used in conventional procedures such as column chromatography or centrifugation and any desired size, shape, porosity, texture, density, and composition, selected from a wide variety of known materials to suit the specific assay configuration, can be used. For example, both controlled pore hollow fiber bundles of polysulfone or porous high density polyethylene rods (available from Porex ® Technologies, Inc., Fairburn, Ga.) can be used conveniently for the immobilization of antibodies and would also provide acceptable physical properties.

Organic solid phases should have surface functional groups such as epoxy, amino, imino, carboxyl, aryl, halosulfonyl, sulfhydryl, which can react with homo- or hetero-bifunctional reagents. These bifunctional reagents can be reacted with the desired anit-CK antibody before or after exposure to the solid phase. Alternatively, reactive groups on the surface of organic solid phase can be reacted directly in a controlled fashion with native or partial anti-CK sub-unit antibodies. The antibody can be attached directly to the solid phase or through linker groups. Typical linking chemistries are known and are discussed in detail in Methods in Enzymology, Volume XLIV., 1976, Section II.A. Immobilization Techniques, Covalent Coupling, Mosbach, K. (ed.) Academic Press, New York, pp. 11–133.

Inorganic solid phases can include silicaceous materials such as glass, silica, bentonite, and metal oxides of iron, nickel, titanium, chromium, etc. One particular advantage of selected metal oxides of iron and chromium is their magnetic properties that allow magnetic separations of solid phases from reaction mixtures. These magnetic properties can be paramagnetic and ferromagnetic. Each of these solid phases can be treated by known methods to coat their surfaces for linking proteins, see, for example, U.S. Pat. No. 3,652,761, issued Mar. 28, 1972, to Weetall et al., incorporated herein by reference. Silicaceous hydroxyl groups can be silanized by a variety of agents having groups capable of forming amide, ester, ether, disulfide and sulfonamide linkages with antibody.

A preferred solid phase for use in the present invention is the surface stabilized (protected) chromium dioxide ($CrO_2$) particles described in applicant's assignee's, E. I. du Pont de Nemours and Company, copending application, Ser. No. 841,107, filed Mar. 18, 1986, incorporated herein by reference.

The protected $CrO_2$ particles have the following properties:
- low remanent magnetism and favorable surface structure—allowing repeated magnetic separation/dispersion cycles;
- rapid separation in a magnetic field;
- high surface area for high capture capacity;
- a highly stable particle for maximum reagent shelf life.

The magnetic particles are sufficiently hydrolytically stable to be useful as solid supports in heterogeneous immunoassays and bioaffinity separations. The core of the particles is acicular, rutile chromium dioxide. This material and its preparation are described in U.S. Pat. Nos. 2,923,683, 4,524,008 and 3,512,930 which are incorporated by reference. The chromium dioxide particles have a surface area of 5–100 $m^2/g$, coercivity of 100–750 oersteds, remanent magnetization of 5–45 emu/g and saturation magnetization of 8–85 emu/g. These particles are surface stabilized as taught in U.S. Pat. No. 3,512,930. The stabilized surface layer is characterized by its X-ray diffraction pattern which exhibits a line corresponding to an interplanar spacing of 316.8 pm.

The chromium dioxide particles are further stabilized with a coating of $SiO_2$. The weight of $SiO_2$ coating the particles is greater than about 1% and preferably from 2–6% of the weight of the chromium dioxide.

The silica coated chromium dioxide is then further coated with a silane to both further stabilize the particle and to provide binding sites for proteins. The technique of attaching antibodies to inorganic supports using silanes is taught in U.S. Pat. Nos. 3,652,761 and 3,933,997. The choice of silane is dictated by the need to bind proteins to the magnetic particle, and a wide variety of such compounds are available.

The magnetic particle when coated with silica and silanized has a particle size of 0.5 l to 5 μm and a remanent magnetization of 8 to 21 emu. The particles are first reduced, as follows: Two hundred fifty grams of upgraded $CrO_2$ particles is milled with 100 g of sodium bisulfite in 1.75 L water for an hour at room temperature. The mixture is then aged for about a week in a closed storage container. This reductive surface treatment converts a large portion of each ferromagnetic core to the nonmagnetic $Cr^{+3}$ layer, which reduces magnetic interactions between particles and lowers retentivity to the extent that the particles become redispersible upon repeated exposure to magnetic field. The particles are dialyzed against water to remove the excess salt and stored as spray dried powder or used immediately. Magnetic separation is avoided throughout the process to minimize magnetic aggregation. Centrifugation or filtration is also avoided to prevent excessive irreversible agglomeration.

To stabilize the core particles against reoxidation, silica is deposited on the $CrO_2$ according to the process set out in U.S. Pat. No. 3,437,507. In a preferred embodiment the $CrO_2$ is first conditioned with a small amount of alumina which provides better deposition on the silica. Still more preferred is the incorporation of a small amount of $B_2O_3$ in the $SiO_2$ layer. The weight ratio of alumina to $CrO_2$ in the solution used to coat the preferred particle is from 0.001–0.1, and the weight ratio of $B_2O_3$ to $SiO_2$ in the solution is from 0.01–0.12. More preferred is an $Al_2O_3/CrO_2$ ratio of 0.005–0.04, a $B_2O_3/SiO_2$ ratio of 0.12 and a $SiO_2/CrO_2$ ratio of 0.05–0.12. The foregoing ratios refer to weights of $Al_2O_3$, $B_2O_3$ and $SiO_2$ in solution and weight of $CrO_2$ particles to be coated. A preferred particle is prepared as follows: One hundred grams of surface reduced $CrO_2$ particles suspended in 2.5 L water is heated to about 70°–90° C. with constant mechanical stirring. To this is added 5.0 mL of 40% to sodium aluminate ($NaAlO_2$) solution and the pH of the suspension adjusted to 9.0 with 2N sodium hydroxide. While stirring, 150 mL of a reagent containing 25 g of sodium metasilicate ($Na_2SiO_3$) and 6.25 g of sodium borate ($Na_2B_2O_4.8H_2O$) is added dropwise over an hour period. The pH of the mixture is maintained at 9.0 by simultaneous dropwise addition of 5% sulfuric acid. The mixture is stirred for another 30 minutes at about 70°–90° C. to cure the particles. The pH is adjusted back to 7.0 with 5% sulfuric acid, cooled and the particles are dialized against water.

Silane coating of the surface reduced, silica coated $CrO_2$ can be carried out in an aqueous or nonaqueous system but the preferred process is the aqueous phase silanization in which silane itself serves as a base catalyst. This works especially well with silanes containing amino functional groups such as 3-aminopropyltriethoxysilane. The reaction involves two steps that can occur in sequence or simultaneously. First is rapid hydrolysis of 3-aminopropyltriethoxysilane to the corresponding silanol and subsequent base catalyzed condensation to form a polymerized siloxane. The second is deposition of the silanol and polymerized siloxane onto the hydroxyl surface of the particles with subsequent covalent bond formation. One hundred grams of the surface reduced, silica coated particles suspended in 1.8 L water is dispersed with an overhead mechanical stirrer and heated to 55° C. To this is added 200 mL of 3-aminopropyltriethoxysilane and the suspension is stirred mechanically for 12 to 18 hours at about 55° C. Maintaining adequate dispersion is critical at this stage to minimize the agglomerate size. Alternatively, ball mill or sand mill silanization is equally effective in producing the finely dispersed particles. The silanized particles are extensively washed with water at room temperature. The finished particles have a mean volume diameter of less than 10 μm as measured by the light scattering technique on a Microtrac® [Particle Size Analyzer (Leeds & Northrup Instruments, North Wales, PA)], and a settling time of less than 20 minutes. The magnetic separation time in a 1000 gauss field with a one centimeter gap is less than 3 minutes. The particles are extensively washed to ensure removal of all adsorbed silane and stored as a 5% suspension in a 10 mM phosphate buffer, pH 7.4.

The immunoassay of the present invention is a heterogeneous immunoassay performed by sequential contact of appropriate reagent mixtures with a solid phase having anti-CK-M or CK-B antibodies attached on its surface. A clinical sample containing mixtures of CK isoenzymes is contacted with the solid phase over an interval appropriate to allow binding to occur. The solid phase is removed from the reaction mixture or the reaction mixture can be removed from the solid phase at specified intervals after reactions have been allowed to take place. Specifically, the biological sample suspected of containing CK-MB is contacted with the solid phase bearing anti-CK-M or CK-B antibodies to form a first reaction mixture. The mixture is allowed to react for from one minute to one hour, preferably from 5 to 30 minutes, at between 5° to 50° C., preferably from 25° to 40° C., to insure that substantially all CK-M or CK-B sub-units, respectively, in the biological sample are bound to immobilized antibody. The solid phase can be separated from the reaction mixture by any convenient means followed by washing with buffer to remove sample constituents and contaminants not bound to the solid phase. The washed solid phase is then contacted with a soluble anti-CK-M or CK-B antibody, having the same sub-unit specificity as that bound to the solid support, to form a second reaction mixture. The immobilized and soluble anti-CK antibodies can be the same or different, as long as they are capable of binding the appropriate CK sub-unit and of substantially completely inhibiting its enzymatic activity. The soluble antibody is allowed to react with the bound CK-MM or CK-BB isoenzyme to inhibit any remaining M or B sub-unit activity, respectively. The solid phase can be but does not have to be separated from the second reaction mixture and washed with water or an appropriate buffer to remove any soluble anti-CK antibody. It is then contacted with an appropriate substrate for the determination of CK isoenzyme activity. The substrate is selected to produce a detectable signal and can be chromogenic, fluorogenic, chemiluminogenic, etc. The detectable signal can be produced directly by the CK activity on the substrate, or indirectly by the activity of other reagents that depend for their activity upon the activity of CK isoenzymes. These substrate reagents are known and are described in detail in U.S. Pat. No. 4,260,678, issued Apr. 7, 1981 to Lepp et al.

Among the advantages realized by the immunoassay of this invention are the removal of contaminating CK fragments (mitochondrial CK, etc.) and other enzymes such as adenylate kinase, present in biological samples which are capable of interfering in the enzymatic determination of CK-MB activity. Also, any contribution to the enzymatic activity of CK-MB during the assay from CK-MM or CK-BB sub-units is eliminated by the anti-CK-M or anti-CK-B immunoinhibiting antibody, respectively. The result is a more specific immunoinhibition assay of CK-MB activity which requires only one antibody, one activity measurement on a given sample, and eliminates the need for the extended reaction times typically required in immunoprecipitation techniques.

The following examples illustrate the invention:

EXAMPLE 1

A. Covalent Coupling of Anit-CK-M Activity Inhibiting Antibody to Magnetic Particles Preliminary washing of the magnetic particles is performed by placing 10 mL of a 5% solids suspension of superparamagnetic Bio Mag ® magnetic particles (silanized mixture of $Fe^{+2}$ and $Fe^{+3}$ oxides, particle diameter 0.1–1.5μ, surface area 100–150 m²/g. Advanced Magnetics Co., Inc., Boston, MA) into a 50 mL tissue culture T-flask and adding 40 mL of a 0.01M $K_2HPO_4$, pH 7.0 (coupling buffer). The suspension is manually shaken for 10 seconds and the flask placed on a permanent magnet for 10 minutes to separate the particles from the liquid phase. This process was repeated an additional two times with 50 mL coupling buffer to complete the washing procedure.

The washed particles were suspended in 20 mL of 5% (w/v) aqueous glutaraldehyde and manually shaken for 10 seconds and then for 1 hour on a rocking platform in a fume hood. Particle separation was effected as previously described, the glutaraldehyde solution discarded, and the particles washed twice in coupling buffer as previously described. The gluteraldehyde activated particles were then suspended in 10 mL of coupling buffer containing 3.2 mg/mL of activity inhibiting anti-CK-M antibody (E. M. Science, Gibbstown, New Jersey). The mixture of the activated magnetic particles and antibody was agitated on a rocking platform at room temperature for 20 hours. Separation of the magnetic particles from the liquid phase was effected as previously described and the supernatant discarded. A 1M glycine, pH 8.0 blocking solution was added (50 mL) to suspend the particles, and the suspension was incubated for 1 hour at room temperature on a rocking platform to block remaining reactive groups. The blocking solution was discarded after magnetic separation and the particles washed three times by repeated suspension in 50 mL 0.01M $K_2HPO_4$, 0.1% human serum albumin (HSA), pH 7.4 (wash buffer), magnetic separation, and removal of the liquid phase. The washed particles were suspended in 10 mL wash buffer for use or storage at 4° C.

B. Determination of CK-MB Activity in Biological Samples

Samples were prepared in both pooled normal human serum and calibrator base material. CK-MB activity levels of 0, 25, 50, 125, and 250 units/L were prepared by adding purified Cynomolgus monkey heart CK-MB concentrate to the serum or calibrator base. Samples containing elevated CK-MM or CK-BB were prepared in serum by adding either purified Cynomolgus monkey heart CK-MM concentrate or purified human brain CK-BB concentrate (Calbiochem Behring; San Diego, CA) to produce activities of 700 units/L CK-MM and 100 units/L CK-BB, respectively. The calibrator base material was obtained by delipifying serum using the mixed ion exchange process described in U.S. Pat. No. 4,264,471, to Briggs et al., incorporated herein by reference, and contained no CK activity. The pooled normal human serum contained 200 U/L natural CK-MM activity. CK values were determined using the CK method on the aca ® discrete clinical analyzer (a registered trademark of E. I. du Pont de Nemours and Company).

The assay was performed by combining and mixing in a test tube, 500 μL of the appropriate sample or control solution and 200 μL of the magnetic particle/anti-CK-M reagent prepared in Part A above, and allowing this mixture to incubate at 37° C. for 10 minutes. The tube was inserted in a test tube rack equipped with a series of permanent magnets on both sides of each individual tube insert area for 1 minute, after which the supernatant was withdrawn and disgarded. The magnetic particle reagent was washed twice with 1 mL wash buffer (0.045M phospate, 0.000039M ethylene-diaminetetraacetic acid (EDTA), 0.2M sodium chloride, 0.00056M mercaptoethanol; pH 7.0) as previously described. The particles were suspended in 100 μL wash buffer and 25 μL of a solution containing 20 mg/mL anti-CK-M antibody (E. M. Science), 376 U/mL yeast hexose kinase (Boehringer-Mannheim Corp.), 224 U/mL bacterial glucose-6-phospate dehydrogenase (Boehringer-Mannheim Corp.), stabilizers and microbial inhibitors. This suspension was mixed by gently rotating the tube several times and incubated at 37° C. for 5 minutes. A 3.4-mL quantity of development reagent was added to the tube with mixing and the mixture allowed to incubate at 37° C. for a period of 10 minutes. The development reagent consisted of 16 mg creatine phosphate, 10 mg glucose, 5 mg nicotinamide adenine dinucleotide (NAD+), 23 mg magnesium acetate, 7.1 mg dithioerythritol (DTE), 9.1 mg adenosine diphosphate (ADP), 6.1 mg adenosine monophosphate (AMP), 0.025 mg $P_1$, $P_5$-diadenosine-5-diphosphate (Ap5A), and 50.6 mg N-2-acetamido-2-aminoethane sulfonic acid (ACES), dissolved in 4.1 mL distilled water. The pH of the development reagent was 6.8.

After 3 minutes of incubation, a first 1.7mL aliquot was removed and placed in a test tube immersed in an ice-water bath and in a permanent magnetic field for 1 minute. During this interval the majority of particles were magnetically separated from the suspension. The supernatant was transferred to a 1-cm cuvette and inserted into a Hewlett Packard Model 8451A spectrophotometer whose cuvette holder had been modified to contain permanent magnets on both sides of the cuvette. The absorbance was determined at 340 nm.

A second aliquot was withdrawn after 10 minutes of incubation and processed in the same way as the first aliquot.

The activity of the sample was determined from the absorbance difference of the first and second aliquots. Data are presented in Tables 1 and 2.

TABLE 1

CK-MB IMMUNOINHIBITION ASSAY OF POOLED NORMAL HUMAN SERUM*

| CK-MB Activity | Absorbance (mA) | | |
|---|---|---|---|
| (U/L) | After 3 min. | After 10 min. | Δ mA |
| 0 | 46 | 52 | 6 |
| 25 | 63 | 145 | 82 |
| 50 | 101 | 204 | 103 |
| 125 | 192 | 510 | 318 |
| 250 | 368 | 888 | 520 |

*Normal human serum sample contained 200 U/L CK-MM.

TABLE 2

CK-MB IMMUNOINHIBITION ASSAY OF DELIPIFIED HUMAN SERUM CALIBRATOR

| CK-MB Activity | Absorbance (mA) | | |
|---|---|---|---|
| (U/L) | After 3 min. | After 10 min. | Δ mA |
| 0 | 3 | 3 | 0 |
| 25 | 33 | 97 | 64 |
| 50 | 53 | 189 | 136 |
| 125 | 127 | 425 | 298 |
| 250 | 281 | 869 | 588 |

Serum samples spiked with 500 U/L CK-MM (Total CK-MM=700 U/L) and 100 U/L CK-BB (CK-MN=200 U/L) were processed in the same manner. The increases in absorbance between the 3-minute and 10-minute periods were 17 mA AND 7 mA, respectively.

Calculation of the difference in milliabsorbance units (mA 10 min.-mA 3 min.) of samples at each level, ΔmA, indicates that clinically acceptable standard curves for evaluation for CK-MB activity were obtained in both normal human serum and delipified human serum. The sensitivity of the test is approximately 2 mA per U/L CK-MB. There was no practically significant contribution of any CK-MM and CK-BB in the samples to the total activity, as determined with serum spiked with CK-MM or CK-BB isoenzyme. This absence of CK-MM and CK-BB activity illustrates that the method of this invention is particularly effective in minimizing background signal from the usual interferants in CK-MB assays.

EXAMPLE 2

Magnetic particles with covalently bound activity-inhibiting anti-CK-M antibody were prepared as in Example 1 except that silanized chromium dioxide magnetic particles (E. I. du Pont de Nemours & Co., Wilmington, DE) were used in place of BioMag® magnetic particles. These were prepared as follows:

Reductive Surface Treatment of $CrO_2$

Two hundred and fifty grams of upgraded heated chromium dioxide were mixed with one hundred grams of sodium bisulfite in 1750 mL of water. The mixture was milled in a W-250V-B Vertical Belt-Drive Colloid Mill (Greerco Corporation, Hudson, N.H.) for 45 min. and aged in a glass container for one week. The particles were dialyzed against distilled water to remove the excess sodium bisulfite. The chromate leaching test gave an absorbance=0.03, settling time=12 min.

Silica Coating

One hundred grams of chromium dioxide particles from above were placed in a 3 liter beaker and 2.5 liters of distilled water were added. The particles were heated to 90° C.±2° C. with mechanical stirring. To the mixture was added 5.0 mL of sodium aluminate (40% solution) and the pH of the suspension was adjusted to 9 by the addition of 5% sufluric acid. To this mixture was added 150 mL of water containing 25 grams of sodium metasilicate and 6.25 grams of sodium borate dropwise over a period of one hour. The pH of the mixture was maintained at 9±0.5 with the simultaneous dropwise addition of 5% sulfuric acid. Vigorous stirring was maintained throughout the reaction. After all the reagents were added, the mixture was heated at 90° C. and stirred for an additional 30 min. before the pH was adjusted to 7 with 5% sulfuric acid and allowed to cool to room temperature. The particles were dialyzed against distilled water. The chromate leaching test gave an absorbance=0.03, settling time=15 min. When aliquots were dried and heated at 25° C., 80° C., and 140° C. for 90 min. and then tested, the chromate leaching test gave absorbances=0.1, 0.2 and 0.25, respectively, compared to 0.33, 0.83 and 2.0 for the surfaced reduced particles.

Silane Coating

One hundred grams of silica coated chromium dioxide particles were suspended in 1.8 liters of distilled water in a 2-liter round-bottom flask equipped with a mechanical stirrer, a reflux condensor and a temperature sensor. Two hundred mL of aminopropyltriethoxysilane was added and the mixture was stirred at 55° C. for 18 hours. The particles were washed three times with 13 liters of distilled water by settling and decantation. The washed particles were suspended in 10 mM phosphates buffer (pH 7) at 50 mg/mL. A chromate leaching test gave an absorbance=0.02, the settline time=8 min. When aliquots were dried and heated at 25° C. 80° C. and 140° C. for 90 min and tested, the chromate absorbances=0.05, 0.20 and 0.25, respectively.

Samples were either standards, prepared by adding purified cynomolgus monkey heart CK-MB concentrate to calibrator base as in Example 1A, or individual human serum specimens. Total CK values were determined using Du Pont's aca® discrete clinical analyzer CK method. Electrophoretic determinations were performed by the Cardiotrac ™ CK procedure (Corning Medical, Medfield, MA).

All incubations and separations were done in a specially-designed reaction chamber which contained multiple sites for individual test tubes. Each site consisted of a test tube retaining cup mounted on a remotely-controlled motor, with two permanent magnets mounted in a framework on opposite sides of each retaining cup. When the motor was activated, the cup and test tube oscillated in a rotary direction with sufficient energy to suspend and hold in suspension a mixture of magnetic particles and solution contained in the test tube. When the motor was deactivated, the oscillating rotary motion ceased allowing separation, through action of the magnetic field, of the magnetic particles from the suspending solution. The temperature of the reaction chamber was controlled at 37° C.

The assay was performed by combining in a test tube contained in the reaction chamber 100 μL of the appropriate sample and 100 μL of the magnetic particle—anti Ck-M inhibiting antibody reagent. The mixer was activated and the mixture allowed to incubate for 5 minutes.

The motor was deactivated, the suspension allowed to separate, and the solution withdrawn and discarded. The magnetic particles were washed thrice with 500 μL wash buffer (1% ACES, 0.15% DTE, pH=6.8) by magnetic particle suspension, separation, and supernate aspiration as previously described. The particles were then mixed with 125 μL wash buffer and 6 μL of the enzyme-antibody reagent solution (as described in Example 1B) and incubated, with agitation, for 5 minutes in the reaction chamber. A 125-μL quantity of development reagent was added to the tube and the mixture allowed to incubate.

Each mL of the development reagent contained 4 mg glucose, 10 mg magnesium acetate, 5 mg n-acetyl cysteine, 2 mg NAD+, 5.4 mg creatine phosphate, 1.0 mg AD and 10 mg ACES. The pH of the development reagent was 6.8.

After 3 minutes of incubation, 120 μL of the reaction mixture was transferred to a second test tube which contained 300 μL of water and 60 μL of quench reagent (an 8-fold concentrate of Tandem®-E monoclonal immunoenzymetric assay Quench Reagent, Hybritech, Inc., San Diego, CA). This mixture was briefly mixed and placed in a M4700 magnetic separator (Advanced Magnetics, Inc., Cambrige, MA).

The absorbance of the magnetic particle-free solution was determined at 340 nm and 400 nm in a Hewlett Packard model 8451A spectrophotometer.

A second 120-μL aliquot of the inital reaction mixture was withdrawn after 10 minutes of incubation and processed in the same way as the first aliquot.

The net 7 minute absorbance change for the sample was determined by the equation $mA = (mA_{340} - mA_{400})_{10\ min} - (mA_{340} - mA_{400})_{3\ min}$.

Results from the assay of a series of standards are shown in Table 3. These results demonstrate the linearity of the assay. The sensitivity of the test was approximately 1.5 mA/U/L CK-MB (slope:1.54 mA/U/L); the standard curve intercept was −2.3 mA, and the correlation coefficient was calculated to be 0.99993.

TABLE 3
STANDARD CURVE REPONSE

| Standard CK-MB Activity (U/L) | Absorbance Change (Δ mA) |
|---|---|
| 0 | 0 |
| 6 | 8 |
| 14 | 18 |
| 25 | 35 |
| 52 | 76 |
| 109 | 165 |
| 219 | 335 |

Table 4 shows assay results of individual human serum specimens. Total CK values were determined by Du Pont's aca® discrete clinical analyzer CK method. Electrophoresis was performed by the Cardiotrac ™ CK method (Corning Medical, Medfield, MA). CK-MB activity was calculated from the difference in milliabsorbance (Δ, unit:mA) using the equation:

$$CK-MB\ activity\ (U/L) = \frac{\Delta\text{-intercept}}{\text{slope}}.$$

These results illustrate that the assay of this invention is both sensitive and specific for CK-MB and that the effects of the usual interferants in CK-MB determinations, such as CK-MM, CK-BB and atypical CK-MM, are minimized.

TABLE 4
CK-MB ASSAY OF INDIVIDUAL HUMAN SPECIMENS

| Sample* | Total CK (U/L) | Electrophoresis (% MB) | CK-MB (U/L) |
|---|---|---|---|
| 1 N | 56 | 0 | 3 |
| 2 N | 127 | 0 | 5 |
| 3 N | 25 | 0 | 2 |
| 4 N | 212 | 0 | 9 |
| 5 N | 70 | 0 | 4 |
| 6 N | 397 | 0 | 9 |
| 7 S | 228 | 0 | 5 |
| 8 S | 138 | 0 | 4 |
| 9 N | 125 | 0 | 6 |
| 10 S | 128 | 0 | 1 |
| 11 N** | 125 | 0 | 5 |
| 12 S | 42 | 0 | 2 |
| 13 S*** | 44 | 0 | 5 |
| 14 S | 99 | 7 | 10 |
| 15 O | 291 | 7 | 23 |
| 16 O | 261 | 8 | 26 |
| 17 O | 245 | 5 | 27 |
| 18 O | 235 | 4 | 19 |
| 19 + | 231 | 4 | 23 |
| 20 + | 160 | 15 | 20 |
| 21 S | 829 | 6 | 25 |
| 22 O | 526 | 16 | 73 |
| 23 + | 1306 | 17 | 96 |
| 24 O | 810 | 7 | 37 |

*"N" indicates serum sample from "normal" healthy human
"S" indicates serum sample from a surgery patient (other than heart)
"O" indicates serum sample from open-heart surgery patient
"+" indicates serum sample from patient with diagnosed myocardial infarction
**Sample contained CK-BB, 5 U/L and atypical CK-MM, 50 U/L
***Sample was lipemic

EXAMPLE 3

Magnetic particle-anti-CK-M inhibiting antibody reagent, samples, and assay equipment were as described in Example 2.

The assay was performed by combining in a first test tube 100 μL of sample and 60 μL of magnetic particle reagent. Incubation proceeded for 5 minutes, after which 90 μL of wash buffer (5% ACES, 0.75% NAC, 0.1% sodium azide, pH=6.75) and 360 μL of deionized water were added. The suspension was mixed, separated and the liquid phase discarded. The particles were washed two additional times. After the final wash, the following reagents were added sequentially:

(1) 15 μL of enzyme-antibody reagent (containing 8 mg anti-CK-M antibody, 90 units yeast hexose kinase, 54 units bacterial glucose-6-phosphate dehydrogenase, stabilizers and microbial inhibitor per mL),
(2) 30 μL of wash buffer (described above),
(3) 120 μL of deionized water, and
(4) 100 μL substrate reagent (containing 25 mM ACES buffer, 6 μM diadenosine pentaphosphate, 1.5 mM NAD+, 15 mM NAC, 20 mM magnesium acetate, 12 mM glucose, 1.44 mM ADP, 13 mM creatine phosphate, 5.4 mM EDTA, and 90 mM trehalose, pH=6.75).

The mixture was incubated with mixing, and aliquots withdrawn, quenched and measured as in Example 2.

This example illustrates an even more efficient means of performing the wash steps, reagent addition and the fact that the inclusion of diadenosine pentaphosphate in the substrate reagent eliminates interference, presumably from adenylate kinase. This interference was due to nonspecific binding to the solid support in hemolyzed specimens. Results of individual human serum specimens tested by this procedure, and that of Example 2, are presented in Table 5:

TABLE 5

CK-MB ASSAY OF INDIVIDUAL HUMAN SERUM SPECIMENS

| | CK-MB (U/L) | |
|---|---|---|
| Sample* | Example 2 Protocol | Example 3 Protocol |
| 1 N | 9 | 9 |
| 2 S | 5 | 5 |
| 3 S | 11 | 9 |
| 4 O | 7 | 8 |
| 5 N** | 23 | 3 |
| 6 N** | 27 | 3 |
| 7 N** | 11 | 6 |

*"N" denotes serum from a "normal" person
"S" denotes serum from a surgery patient
"O" denotes serum from an open-heart surgery patient
**Samples were visibly hemolyzed

I claim:

1. An immunoinhibition assay for CK-MB comprising the steps of:
   (a) forming a first reaction mixture by contacting a liquid sample suspected of containing CK-MB isoenzyme with a molar excess of anti-CK-M sub-unit antibody immobilized on a solid phase, said antibody being capable of substantially completely inhibiting the enzymatic activity of the CK-M sub-unit;
   (b) allowing a reaction to occur whereby complexes are formed between M sub-unit-containing isoenzymes and the immobilized antibody;
   (c) separating the solid phase from the reaction mixture;
   (d) forming a second reaction mixture by contacting the solid phase with a soluble anti-CK-M sub-unit antibody capable of substantially completely inhibiting the enzymatic activity of the CK-M sub-unit; and
   (e) determining the enzymatic activity of the uninhibited isoenzyme CK-B sub-unit associated with the solid phase.

2. The immunoinhibition assay of claim 1 wherein the antibody is immobilized on said solid phase through covalent bonding.

3. The immunoinhibition assay of claim 1 wherein the solid phase is inorganic.

4. The immunoinhibition assay of claim 3 wherein the solid phase is magnetic.

5. The immunoinhibition assay of claim 3 wherein the solid phase is surface reduced, silica coated, silanized $CrO_2$.

6. The immunoinhibition assay of claim 1 wherein the solid phase is organic.

7. The immunoinhibition assay of claim 3 wherein the solid phase is coated with agents having groups capable of forming linkages with antibodies.

8. The immunoinhibition assay of claim 3 wherein the solid phase is silanized.

9. The immunoinhibition assay of claim 1 wherein the solid phase is separated from the reaction mixture in step (c) magnetically.

10. The immunoinhibition assay of claim 1 wherein the enzymatic activity determination is carried out in the presence of diadenosine pentaphosphate.

11. The immunoinhibition assay of claim 10 wherein the solid phase is silanized chromium dioxide and wherein the solid phase is separated from the reaction mixture magnetically.

12. An immunoinhibition assay for CK-MB comprising the steps of:
   (a) forming a first reaction mixture by contacting a liquid sample suspected of containing CK-MB isoenzyme with a molar excess of anti-CK-B sub-unit antibody immobilized on a solid phase, said antibody being capable of substantially completely inhibiting the enzymatic activity of the CK-B sub-unit;
   (b) allowing a reaction to occur whereby complexes are formed between B sub-unit-containing isoenzymes and the immobilized antibody;
   (c) separating the solid phase from the reaction mixture;
   (d) forming a second reaction mixture by contacting the solid phase with a soluble anti-CK-B sub-unit antibody capable of substantially completely inhibiting the enzymatic activity of the CK-B sub-unit; and
   (e) determining the enzymatic activity of the uninhibited isoenzyme CK-M sub-unit associated with the solid phase.

13. The immunoinhibition assay of claim 12 wherein the antibody is immobilized on said solid phase through covalent bonding.

14. The immunoinhibition assay of claim 12 wherein the solid phase is inorganic.

15. The immunoinhibition assay of claim 14 wherein the solid phase is magnetic.

16. The immunoinhibition assay of claim 14 wherein the solid phase is surface reduced, silica coated, silanized $CrO_2$.

17. The immunoinhibition assay of claim 12 wherein the solid phase is organic.

18. The immunoinhibition assay of claim 14 wherein the solid phase is coated with agents having groups capable of forming linkages with antibodies.

19. The immunoinhibition assay of claim 14 wherein the solid phase is silanized.

20. The immunoinhibition assay of claim 12 wherein the solid phase is separated from the reaction mixture in step (c) magnetically.

21. The immunoinhibition assay of claim 12 wherein the enzymatic activity determination is carried out in the presence of diadenosine penta-phosphate.

22. The immunoinhibition assay of claim 21 wherein the solid phase is silanized chromium dioxide and wherein the solid phase is separated from the reaction mixture magnetically.

* * * * *